US00PP26783P3

(12) United States Plant Patent

Klemm et al.

(10) Patent No.: US PP26,783 P3

(45) Date of Patent: May 31, 2016

(54) *PETUNIA* PLANT NAMED 'KLEPH13235'

(50) Latin Name: *Petunia hybrida*
Varietal Denomination: KLEPH13235

(71) Applicant: Klemm+Sohn GmbH & Co. KG, Stuttgart (DE)

(72) Inventors: Nils Klemm, Stuttgart (DE); Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 141 days.

(21) Appl. No.: 14/120,062

(22) Filed: Apr. 21, 2014

(65) Prior Publication Data

US 2015/0305218 P1 Oct. 22, 2015

(51) Int. Cl.
*A01H 5/02* (2006.01)

(52) U.S. Cl.
USPC ..... Plt./356.2

(58) Field of Classification Search
USPC ..... Plt./356.2
See application file for complete search history.

*Primary Examiner* — Keith Robinson

(74) *Attorney, Agent, or Firm* — Barbara Campbell; Bethany R. Roahrig; Cochran Freund & Young, LLC

(57) ABSTRACT

A new *Petunia* plant particularly distinguished by light violet, double flowers, a medium form, and a mounding and upright plant habit, is disclosed.

1 Drawing Sheet

Genus and species: *Petunia hybrida.*
Variety denomination: 'KLEPH13235'.

BACKGROUND OF THE NEW PLANT

The present invention comprises a new and distinct variety of *Petunia*, botanically known as *Petunia hybrida*, and hereinafter referred to by the variety name 'KLEPH13235'. 'KLEPH13235' originated from a cross-pollination conducted in July 2009 in Latina, Italy between the proprietary female *Petunia* variety 'PH-2008-0221' (unpatented) and the male *Petunia* variety 'PH-2009-0893' (unpatented).

The seeds from the cross were sown and plants were grown in a greenhouse for evaluation, where an individual plant designated 'KLEPH13235' was selected from the group in April 2010 of plants in Latina, Italy having light violet, double flowers. In April 2010, 'KLEPH13235' was first vegetatively propagated by terminal tip cuttings and tissue culture in Latina, Italy. 'KLEPH13235' was found to reproduce true to type in successive generations of asexual propagation via tissue culture and terminal tip cuttings.

SUMMARY

The following are the most outstanding and distinguishing characteristics of this new variety when grown under normal horticultural practices in Stuttgart, Germany and Latina, Italy.

1. Light violet, double flowers;
2. A medium form; and
3. A mounding and upright plant habit.

CROSS REFERENCE TO RELATED APPLICATIONS

Plant Breeders Rights for this variety have been filed with the European Community Plant Variety Rights Office on Feb. 2, 2014, Application No. 2014/0337 and in Canada on Feb. 18, 2014, Application No. 14-8213. 'KLEPH13235' has not been sold or made publicly available more than one year prior to the filing of the instant application.

DESCRIPTION OF THE PHOTOGRAPH

This new *Petunia* plant is illustrated by the accompanying photograph of a plant grown in a glass greenhouse in Stuttgart, Germany. The photograph was taken in May 2013 and shows the foliage and flowers of a 3-month-old plant grown in a pot. The colors shown are as true as can be reasonably obtained by conventional photographic procedures.

DESCRIPTION OF THE NEW VARIETY

The following detailed descriptions set forth the distinctive characteristics of 'KLEPH13235'. The data which define these characteristics were collected from asexual reproductions carried out in Latina, Italy. Data was collected on plants grown 14-weeks from cultivation from potting in a plastic greenhouse in Latina, Italy in March 2014. Color references are to The R.H.S. Colour Chart of The Royal Horticultural Society of London (R.H.S.), 5$^{th}$ edition (2007).

Classification:
- *Family.*—Solanaceae.
- *Botanical.*—*Petunia hybrida.*
- *Common.*—*Petunia.*
- *Designation.*—'KLEPH13235'.

Parentage:
- *Female parent.*—The proprietary female *Petunia* variety 'PH-2008-0221' (unpatented).
- *Male parent.*—The proprietary male *Petunia* variety 'PH-2009-0893' (unpatented).

Plant:
- *Form.*—Medium.
- *Habit.*—Upright-mounding.
- *Height* (*from top of soil*).—15.0 cm.
- *Width* (*horizontal plant diameter*).—25.0 cm.
- *Propagation.*—Terminal tip cuttings and tissue culture.

*Time to produce a finished flowering plant.*—14 weeks in the winter and 8 weeks in the spring.

*Time to initiate and develop roots.*—2 to 3 weeks.

*Root description.*—Moderate density, moderate branching, RHS NN155A white roots.

Stems:

*Average number (basal).*—18.

*Length of basal branches (from the base of the stem to the tip).*—10.0 cm.

*Internode length.*—0.5 cm to 1.0 cm.

*Diameter of branches (from midpoint).*—0.4 cm.

*Stem color.*—RHS 144B.

*Anthocyanin.*—Absent.

*Texture.*—Pubescent.

Leaves:

*Arrangement.*—Alternate at the base of the stems, opposite on the flower stems.

*Length.*—3.5 cm.

*Width.*—3.0 cm.

*Shape.*—Mature leaves are wide-obovate and immature leaves are elliptic.

*Apex.*—Mature leaves are obtuse and immature leaves are acute.

*Base.*—Attenuate.

*Margin.*—Entire.

*Variegation.*—Absent.

*Leaf blade blistering.*—Present.

*Immature and mature leaf color.*—Upper surface: RHS N137B. Lower surface: RHS 137C.

*Texture (both upper and lower surfaces).*—Slightly pubescent.

*Venation pattern.*—Arcuate.

*Venation color.*—Upper surface: RHS 146B. Lower surface: RHS 144B.

*Petioles.*—Length: 0.4 cm. Diameter: 0.2 cm. Color: RHS 144B. Texture: Slightly pubescent.

Flower buds:

*Shape.*—Irregular oblong.

*Length.*—2.5 cm.

*Diameter.*—0.8 cm.

*Color at tight bud.*—RHS N92A and RHS 144A and RHS 144B.

*Texture.*—Slightly pubescent.

Inflorescence:

*Blooming habit (flowering season).*—Permanent flowering during summer time.

*Inflorescence type.*—Cymose.

*Number of flowers per node.*—1.

*Lastingness of individual blooms on the plant.*—7 to 10 days.

*Fragrance.*—Absent.

*Flowers.*—Arrangement: Composed of 14 to 15 petals fused at the base. Shape: Funnel-form. Diameter (flower face): 5.5 cm. Depth (total length of flower): 4.5 cm. Throat/Funnel: Length: 2.5 cm. Diameter (at opening): 1.2 cm. Texture (both inner and outer surfaces): Smooth, glabrous. Color, immature flower: Face/Margin color: RHS 83B. Upper surface: RHS 83B. Lower surface: RHS N82A and RHS N82B. Color, mature flower: Face/Margin color: RHS 83B. Upper surface: RHS 83B. Lower surface: RHS N82A and RHS N82D. Petals: Color: Inner surface: RHS 83B. Outer surface: RHS N82A and RHS N82D. Apex: Slightly mucronate. Base: Irregularly fused. Margin: Irregularly crenate. Strength of waviness: Strong. Degree of lobation: Weak. Surface texture (both surfaces): Smooth, glabrous. Calyx arrangement: Actinomorphic, composed of 5 sepals. Sepals: Color: Upper surface: RHSN N137B. Lower surface: RHS 137C. Length: 1.7 cm. Width: 0.4 cm. Shape: Oblanceolate. Apex: Broadly acute. Base: Attenuate. Margin: Entire. Texture (both upper and lower surfaces): Pubescent.

*Pedicels.*—Color: RHS 144A. Length: 2.5 cm. Diameter: 0.25 cm. Texture: Pubescent.

Reproductive organs:

*Stamens.*—Quantity: 5. Shape: Needle with elliptic-ovate head. Filament: Length: 1.5 cm. Diameter: 0.05 cm. Color: RHS 156A. Anther: Shape: Round-ovate. Color: RHS 4C. Length: 0.25 cm. Diameter: 0.15 cm. Pollen: Amount: Variable. Color: Not available.

*Pistils.*—Quantity per flower: 1. Length: 0.7 cm. Stigma color: RHS N82C. Style color: RHS 1C.

Fruit and seed set: No fruit and seed set observed to date.

Disease and pest/insect resistance: No disease and pest/insect resistance observed to date.

COMPARISON WITH PARENTAL LINES AND KNOWN VARIETY

'KLEPH13235' is a distinct variety of *Petunia* and is distinguished from its parents as described in Table 1.

TABLE 1

Comparison with Parental Lines

| Characteristic | 'KLEPH13235' | Female Parent 'PH-2008-0221' | Male Parent 'PH-2009-0893' |
|---|---|---|---|
| Flower color | Light violet | Salmon-pink | Dark pink-violet |
| Flower type | Double | | Single |

'KLEPH13235' is a distinct variety of *Petunia* and is most similar to the commercial *Petunia* variety 'KLEPH09191' (U.S. Plant Pat. No. 21,994), also commercially known as 'Sweet Sunshine Burgundy'. Differences between the varieties are described in Table 2.

TABLE 2

Comparison with Similar Variety

| Characteristic | 'KLEPH13235' | 'KLEPH09191' |
|---|---|---|
| Flower color | Light violet | Purple-violet |

We claim:

1. A new and distinct variety of *Petunia* plant designated 'KLEPH13235' as illustrated and described herein.

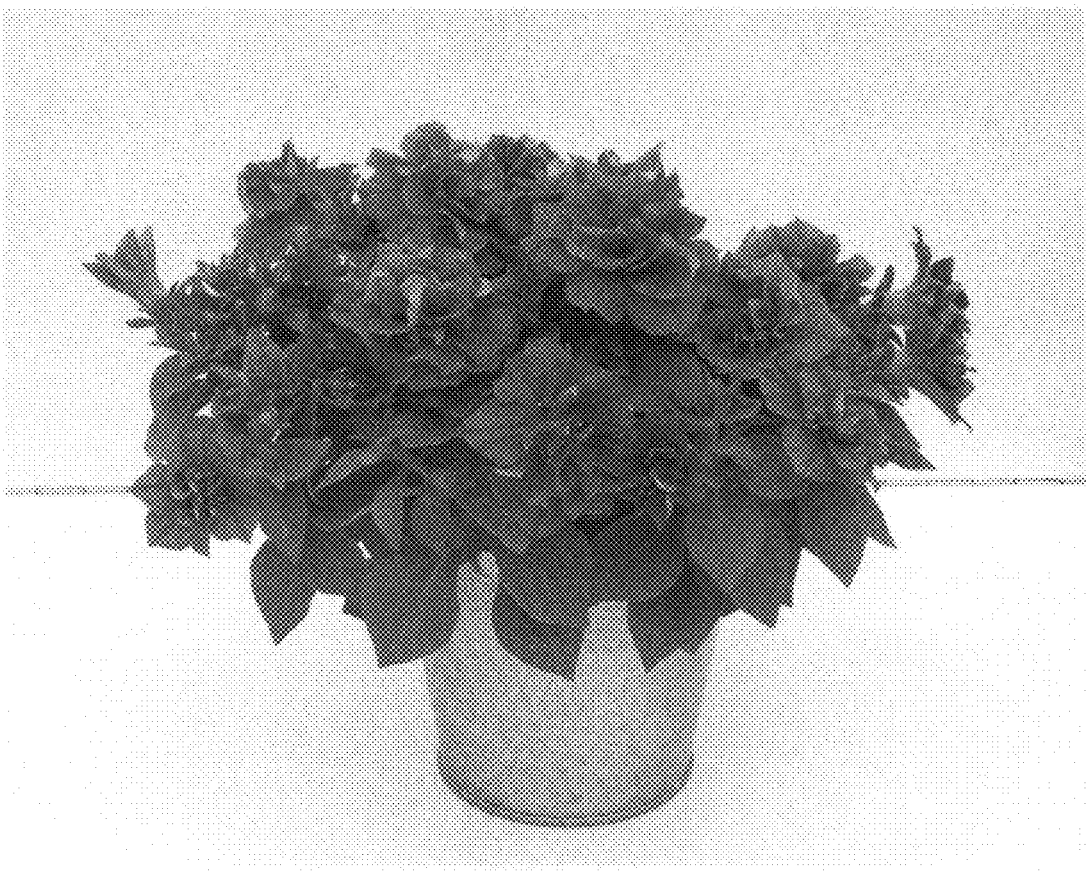

* * * * *